(12) United States Patent
Kuehner et al.

(10) Patent No.: US 7,955,057 B2
(45) Date of Patent: Jun. 7, 2011

(54) MEDICAL PUMP

(75) Inventors: Ralf Kuehner, Stuttgart (DE); Martin Hagg, Wannweil (DE); Jochen Queck, Tubingen (DE)

(73) Assignee: ERBE Elektromedizin GmbH, Tübingen (DE)

( * ) Notice: Subject to any disclaimer, the term of this patent is extended or adjusted under 35 U.S.C. 154(b) by 1201 days.

(21) Appl. No.: 11/630,578

(22) PCT Filed: Jun. 22, 2005

(86) PCT No.: PCT/EP2005/006753
§ 371 (c)(1),
(2), (4) Date: Dec. 22, 2006

(87) PCT Pub. No.: WO2006/002815
PCT Pub. Date: Jan. 12, 2006

(65) Prior Publication Data
US 2008/0038124 A1    Feb. 14, 2008

(30) Foreign Application Priority Data

Jun. 30, 2004  (DE) .................. 10 2004 031 674

(51) Int. Cl.
*F04B 35/01* (2006.01)
*A61B 17/3203* (2006.01)
(52) U.S. Cl. ........ 417/360; 417/238; 417/415; 417/572; 192/48.1; 604/152; 606/167
(58) Field of Classification Search ............ 417/238, 417/413.1, 415, 454, 477.2, 360, 572; 83/177; 192/48.1, 48.2, 48.3, 48.7; 604/152, 154, 604/22, 228; 606/167, 171
See application file for complete search history.

(56) References Cited

U.S. PATENT DOCUMENTS

| 3,692,052 | A | | 9/1972 | Cattanach |
| 3,958,898 | A | | 5/1976 | Abrahams et al. |
| 4,087,213 | A | | 5/1978 | Hadama |
| 5,061,241 | A | | 10/1991 | Stephens, Jr. et al. |
| 5,066,282 | A | | 11/1991 | Wijay et al. |
| 5,295,967 | A | * | 3/1994 | Rondelet et al. ............. 604/154 |
| 5,667,102 | A | | 9/1997 | Keller |
| 5,843,022 | A | | 12/1998 | Willard et al. |
| 6,216,573 | B1 | | 4/2001 | Moutafis et al. |
| 6,368,080 | B1 | | 4/2002 | Sipin |
| 6,382,928 | B1 | | 5/2002 | Chang |

(Continued)

FOREIGN PATENT DOCUMENTS

CN    2075260 U    4/1991

(Continued)

OTHER PUBLICATIONS

Summary for Azzolini IT MO20040028 including publication date of that reference and Abstract of corresponding document Azzolini EP 1561483, Publication date of Aug. 10, 2005.*

(Continued)

*Primary Examiner* — Devon C Kramer
*Assistant Examiner* — Leonard J Weinstein
(74) *Attorney, Agent, or Firm* — Dickstein Shapiro LLP (57) ABSTRACT

The invention relates to a medical pump, especially for water jet surgery, in which a pump unit is assembled as a single use article and can be reversibly connected to a pump actuating device. Within the pump, the pump actuating device is also used to open up the connection between the pump unit and the pump actuating device.

6 Claims, 9 Drawing Sheets

U.S. PATENT DOCUMENTS

| | | |
|---|---|---|
| 6,575,936 B1 * | 6/2003 | Kojima et al. ............ 604/155 |
| 6,592,551 B1 * | 7/2003 | Cobb ...................... 604/155 |
| 6,610,027 B1 | 8/2003 | El Hatu |
| 6,652,006 B1 | 11/2003 | Digiacomo |
| 6,752,789 B2 * | 6/2004 | Duchon et al. ............ 604/228 |
| 7,290,991 B2 | 11/2007 | Staley et al. |
| 7,347,837 B2 * | 3/2008 | Azzolini ................... 604/154 |
| 2002/0025267 A1 * | 2/2002 | Lieber et al. .............. 417/572 |
| 2002/0176788 A1 | 11/2002 | Moutafis et al. |
| 2003/0149402 A1 * | 8/2003 | Gerlach et al. ............ 604/151 |
| 2004/0057854 A1 * | 3/2004 | Wakabayashi et al. ..... 417/448 |
| 2005/0038371 A1 | 2/2005 | Reich et al. |
| 2005/0220639 A1 * | 10/2005 | Sasaki et al. .............. 417/415 |

FOREIGN PATENT DOCUMENTS

| | | |
|---|---|---|
| DE | 42 22 918 | 1/1994 |
| DE | 203 09 616 U | 11/2003 |
| EP | 0 551 920 | 7/1993 |
| EP | 1561483 A1 * | 8/2005 |
| JP | 48-17127 Y1 | 5/1973 |
| JP | 62-85000 A | 4/1987 |
| JP | 2-084068 A | 6/1990 |
| JP | 4-288155 A | 10/1992 |
| JP | 6-192 A | 1/1994 |
| JP | 2000-508247 A | 7/2000 |
| WO | WO 99/33510 | 7/1999 |
| WO | WO 02/095234 | 11/2002 |
| WO | WO 03/013645 | 2/2003 |
| WO | WO 2004/112623 | 12/2004 |
| WO | WO 2005-034777 | 4/2005 |

OTHER PUBLICATIONS

English Translation of the Written Opinion of the International Searching Authority issued in related application PCT/EP2005/006753 (4 pages) (Jan. 2004).

* cited by examiner

MEDICAL PUMP

FIELD OF THE DISCLOSED EMBODIMENTS

The disclosed embodiments relate to a medical pump, in particular for water jet surgery.

BACKGROUND

Water jet surgery has been used for some time in liver surgery, as this organ has tissue structures of different firmness (parenchyma, blood vessels and bile ducts) unlike any other organs and the applied water jet separates the tissue being cut (parenchyma) yet leaves the blood vessels and bile ducts undamaged. Naturally, precise control of the cutting pressure is required for this type of operation.

A further problem with water jet surgery is that the cutting medium must be totally sterile (e.g. Ringer solution), as the liquid comes into contact with body tissue in the closest and most intensive way possible. Ordinary problems such as high reliability, simplicity and economic manufacture must also be considered.

Medical pumps for water jet surgery are known, for example, from U.S. Pat. No. 6,216,573 B1 and DE 203 09 616 U1, which comprise an exchangeable pump unit for single use, which can be connected to pump actuating devices. Changing of the pump devices is, however, very costly with the known setups. As relatively large forces are needed to generate high pressure with sufficient flow, the devices for connection of the pump device to the pump actuating devices must be very substantial so that they can maintain a "firm hold" on the pump device during operation.

SUMMARY

The disclosed embodiments include a medical pump wherein the connection between the pump unit and the pump actuating device is improved and easier to operate.

A medical pump according to disclosed embodiment includes a pump unit which is assembled as a single use article and which comprises at least one piston and piston rod for displacing the piston in an allocated cylinder defined by the pump unit; a pump actuating device comprising at least one controllable drive device and a motor control adapted to actuate the pump unit by displacing the at least one piston rod; holding devices which are adapted to open and close for reversible attachment of the pump unit to the pump actuating device; and clutch means which are adapted to open and close for reversible connection of the at least one piston rod to the at least one controllable drive device, wherein the at least one controllable drive device of the pump actuating device is further adapted to actuate the opening or closing of at least one of said holding devices or said clutch means.

In the disclosed embodiments, the drive device that pushes the piston back and forth additionally actuates or controls the holding devices and/or the clutch means as well. Simple operation by means of the drive device is thus possible and a large holding force can be exerted, as this is applied during opening to decouple the pump unit from the pump actuating device and not by the user.

The holding devices and/or the clutch devices are preferably snap fittings. The snap fittings are constructed so that closing of the holding devices and/or clutch devices can be achieved by snapping the holding devices and/or clutch devices in place and so that opening the holding devices and/or clutch devices can be achieved by means of the drive device opening the snap fittings. The energy required for connecting the pump device to the drive device can be generated very easily by the user. Opening is then carried out by the drive devices with a corresponding large holding force. In this way, only opening must be carried out by the drive devices but not closing as well. This simplifies the setup.

The snap fittings are preferably constructed so that the force required for closing is less than that for opening.

The drive device is preferably constructed so that the engagement devices fitted in the clutch devices are positioned at rest prior to attaching the pump unit to the pump actuating device so that, on connecting the pump unit to the pump actuating device, the engagement devices disengage from the piston rods and the clutch devices can be closed by actuating the drive devices. This means that the user does not have to carry out any great manipulation in relation to the pistons or piston positions in order to attach the pump unit to the pump actuating device.

In one preferred embodiment, two pistons with piston rods are provided in the cylinders and the pump actuating device is constructed to give alternate displacement of the pistons. This arrangement ensures an increased pump performance. In this embodiment, the pump actuating device is constructed either with two motors or a motor with controllable gearing preferably controllable such that the pistons can be displaced in one of two ways: (1) synchronously for alternate opening or closing of the holding device and/or the clutch devices and (2) alternately during normal pump operation. The pistons are operated alternately during (2) normal pump operation. A different modus operandi (e.g., synchronous operation) is selected for opening and closing of the holding device and/or the clutch devices using the same drive set as for normal pump operation. This results in a simplified setup of the pump.

The drive device is preferably a linear drive (or in an embodiment with two pistons, two linear drives) with shaft and motor so that the shaft is drivable in a controllable manner. Very accurate movements can be carried out via such linear drives, thereby protecting the pump with its piston/cylinder units.

The motor control is preferably constructed in such a way that the pistons can be displaced at a constant speed. This results in a smoother delivery of the medium to be pumped.

BRIEF DESCRIPTION OF THE DRAWINGS

Disclosed embodiments are now described by way of example with reference to the accompanying drawings.

DETAILED DESCRIPTION

The same reference numbers will be used for the same parts and for parts with the same function.

Figure 1:
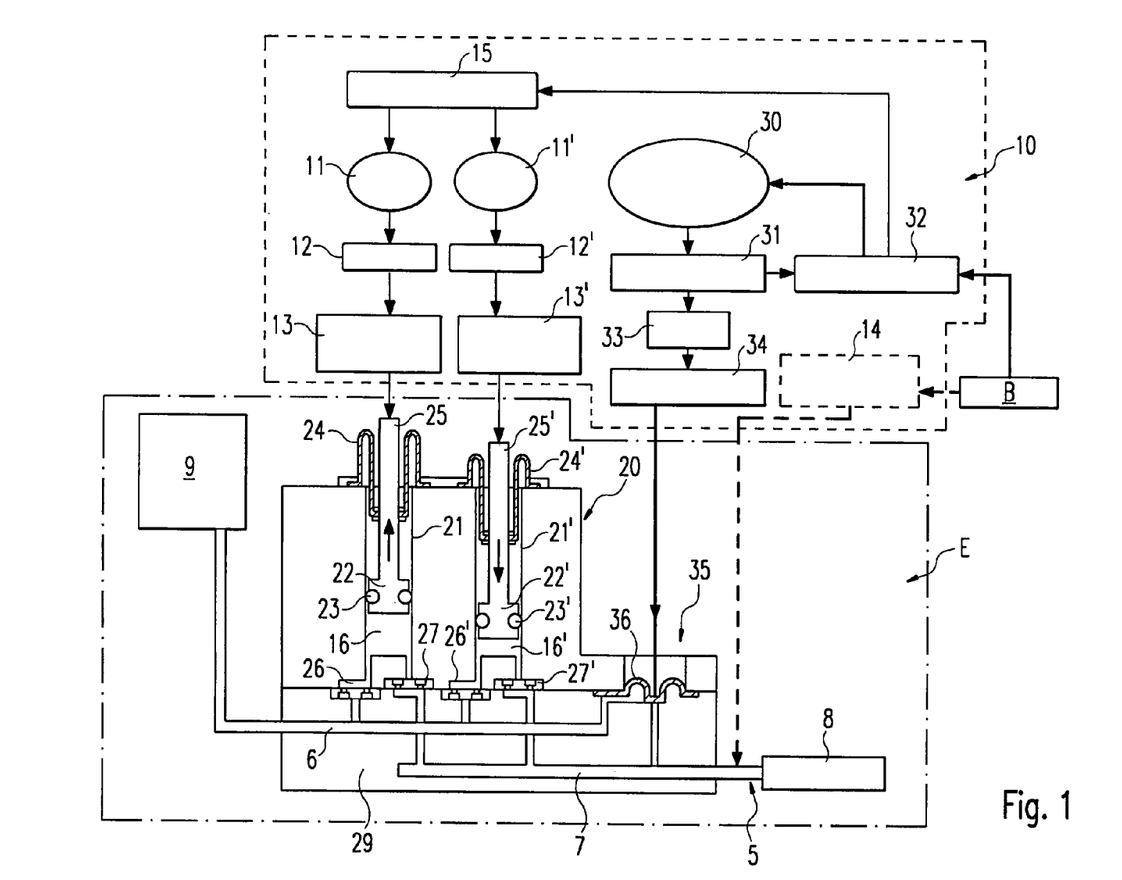
FIG. 1 is a schematic block diagram of a medical pump arrangement according to a disclosed embodiment.

In one disclosed embodiment depicted in FIG. 1 a pump actuating device 10 is provided which encompasses a motor control 15 for the control of two motors 11, 11', which are connected via gearing 12, 12' and clutch devices 13, 13' to the piston rods 25, 25'. Ah operator B can operate the motor control 15 by means of suitable switches (foot switch or finger switch) so that the motors 11, 11' alternately displace the piston rod 25, 25' and thus the pistons 22, 22' in the cylinders 21, 21' of a pump unit 20 via the described train, so that the volume of the pressure chambers 16, 16' of the pump unit 20 is alternately enlarged and reduced.

In order to seal the pressure chambers 16, 16' and the pistons 22, 22' in relation to the cylinders 21, 21' seals 23, 23' are envisaged at the pistons 22, 22'. Moreover, the piston rods 25, 25' maintain sterility with cup seals 24, 24', which are firmly fixed to the cylinders 21, 21' on the one hand and to the pistons rods 25, 25' on the other. In this way germs from the ambient air which, without these cup seals 24, 24', would settle on the internal walls of the cylinders 21, 21' and pass through the seals 23, 23' can neither mix with the working fluid nor find their way into the same.

Suction valves 26, 26' as well as pressure valves 27, 27' are connected to the pressure chambers 16, 16'. The suction valves 26, 26' are connected via a fluid inlet 6 to a reservoir 9 for the working fluid. The pressure valves 27, 27' are connected to the pressure hose 5 which leads to an applicator 8 via a fluid outlet 7. The pump unit 20 forms a disposable part E together with the reservoir 9 including its contents, pressure hose 5 and applicator 8, which is disposed of after each operation, so that the entire setup meets the highest sterility requirements possible.

A butterfly valve 14 is provided by means of which (in addition to the motor control 15) operator B can switch off the fluid flow completely. The embodiment shown in FIG. 1 includes a pressure control valve 35 which with the aid of a valve membrane 36 can open and close a connecting channel between fluid outlet 7 and fluid inlet 6. The membrane 36 is operated by an actuator 30 via a push rod 34 and a spring 33 as well as a dynamometer 31. The dynamometer 31 supplies a power proportional output signal to a controller 32, by means of which an operator B can set a maximum pressure. Instead of a separate dynamometer 31 the operating current of the actuator 30 can be measured which is also power proportional.

This layout means that the fluid pressure can be accurately adjusted at the applicator 8. Moreover, pressure fluctuations resulting from piston operation are smoothed out by the control valve 35. The important point is that the pressure control valve 35 due to its construction operates with the membrane pressurized by fluid in a power-controlled and not a travel-controlled manner. No pressure adjustment error can therefore occur during coupling of the pump unit 20 to the pump actuating device 10 even with dimension tolerances as it is not the geometric dimensions (travel) which are important, but the power with which the pressure control valve 35 is operated.

Figure 2:
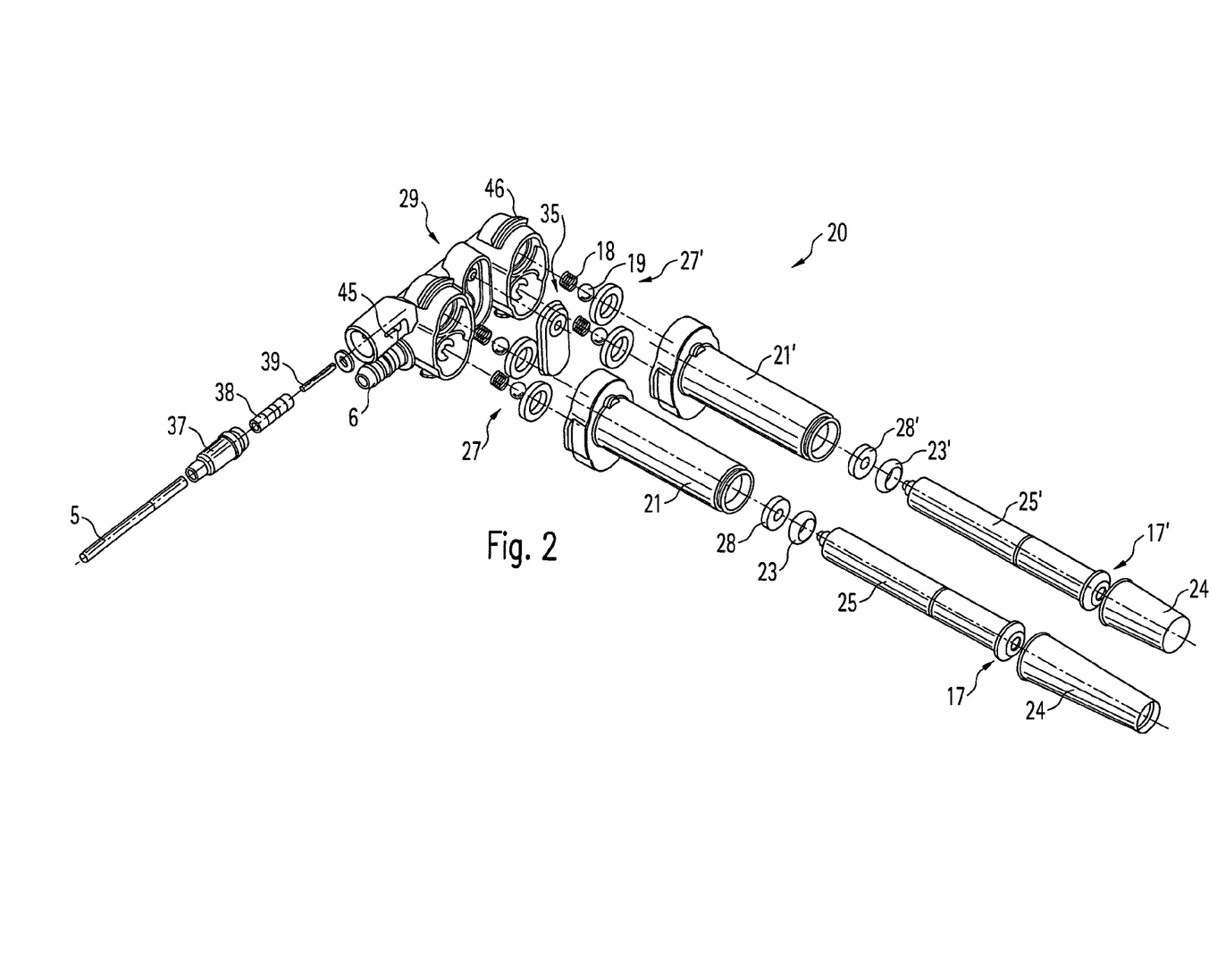
FIG. 2 is an exploded diagram of an embodiment of the pump.

FIG. 2 shows an exploded view of a construction embodiment of the pump device 20. In this embodiment the pressure and suction valves 26/27 encompass balls 19 which are pressed onto the valve seats via springs 18 (not visible in the illustration) which principle is known.

The cylinder head 29 has two sections to which the cylinders 21, 21' are coupled, whereby the valves sit between the cylinders 21, 21' and the cylinder head 29.

It can further be seen from FIG. 2, that the piston rods 25, 25' have coupling projections 17, 17' at their distal ends which serve to create a mechanical connection with the coupling systems 13, 13'.

The pistons in this embodiment are formed by the proximal ends of the piston rods 25, 25' fitted with caps 28, which simultaneously hold seals 23, 23' firmly on the piston rods 25, 25'.

The pressure hose 5 is fastened irreversibly to the cylinder head 29 via a connecting piece 37, a crimping piece 38 and an internal pipe which is inserted into the pressure hose 5, whereby after assembly (in a known way) the connecting piece 37 is held in the cylinder head 29 by means of a catch 45 which holds the connecting piece 37 irreversibly in the cylinder head 29.

Figure 3:
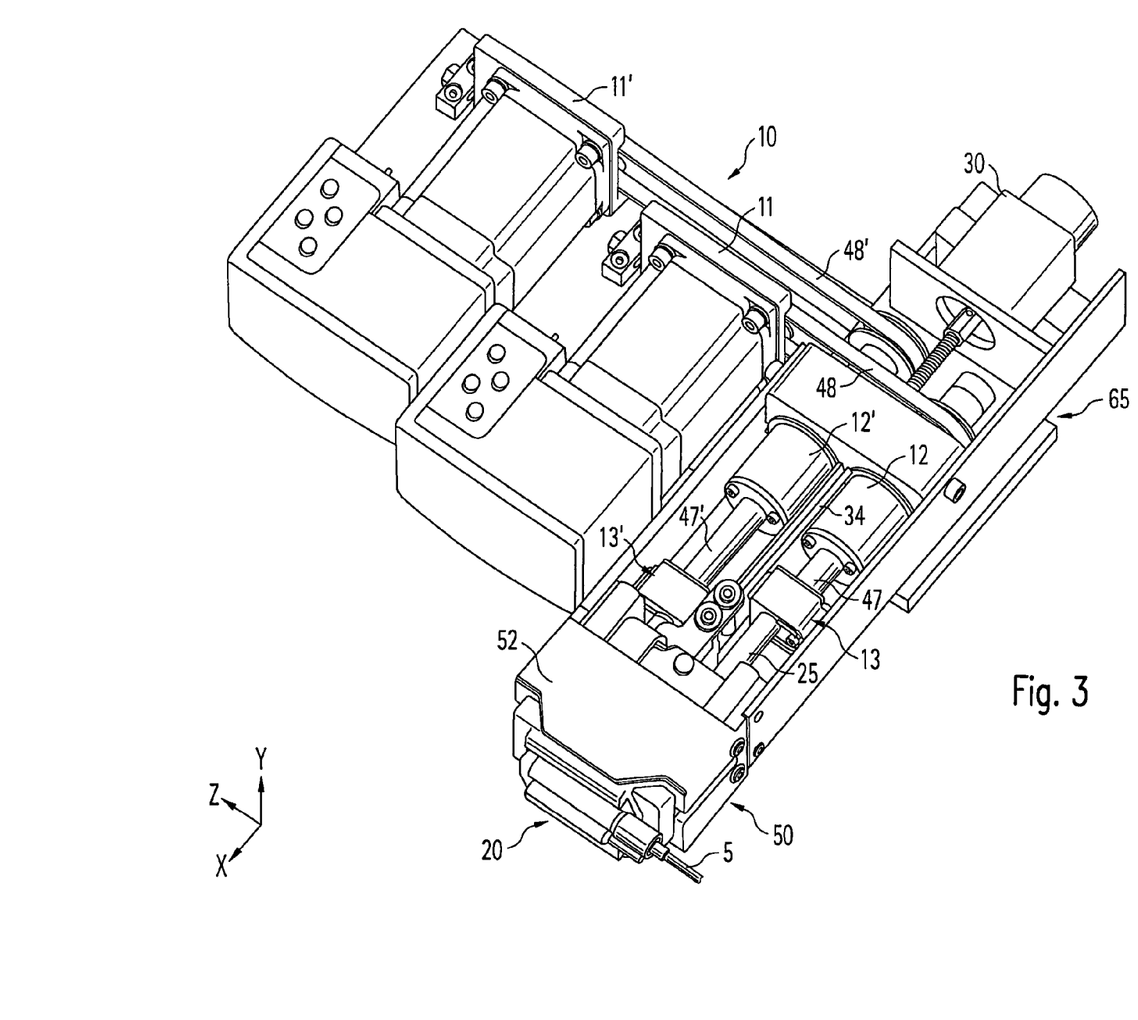
FIG. 3 is a perspective view of the pump actuating device with coupled pump unit.

FIG. 3 shows a perspective illustration of the pump actuating device 10 with a coupled pump unit 20. This illustration shows that the pump actuating device has a frame 65 to which the motors 11, 11' are attached. They are constructed as reversing motors which drive the shafts 47, 47' via cog belts 48, 48' and gearing 12, 12', so that the rotary movement of the motors 11, 11' is translated into a linear movement. Attached to the shafts 47, 47' are the clutches 13, 13' to which the piston rods 25, 25' can be coupled. The setup of the actuator 30 with the relevant push rod 34 is also visible in this illustration.

Moreover, the holding device 50 is attached to the frame 25 which is intended for holding the pump unit 20.

The holding device is explained in more detail with the aid of FIGS. 4-12.

The holding device 50 encompasses jaw holder 52, 52' with jaws 51, 51' at the end, the jaws 51, 51' being are constructed in such a way that they can engage with the lugs 46 (FIG. 2) provided in order to hold the pump unit 20.

Figure 4:
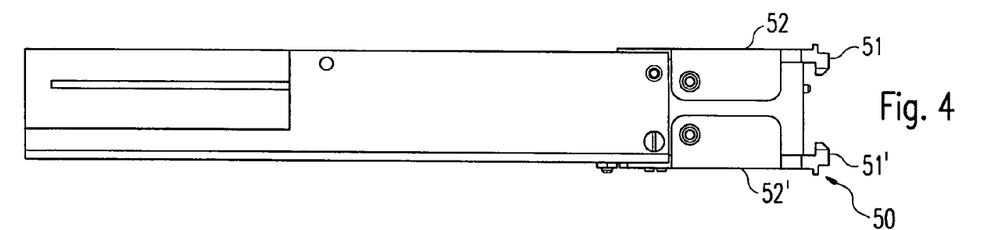
FIG. 4 is a side view of a holding device.
Figure 5:
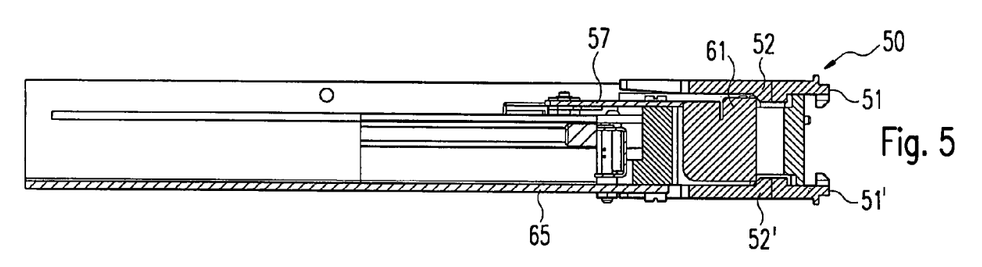
FIG. 5 is a view similar to FIG. 4, partially-sectioned along the line V-V in FIG. 6.
Figure 10:
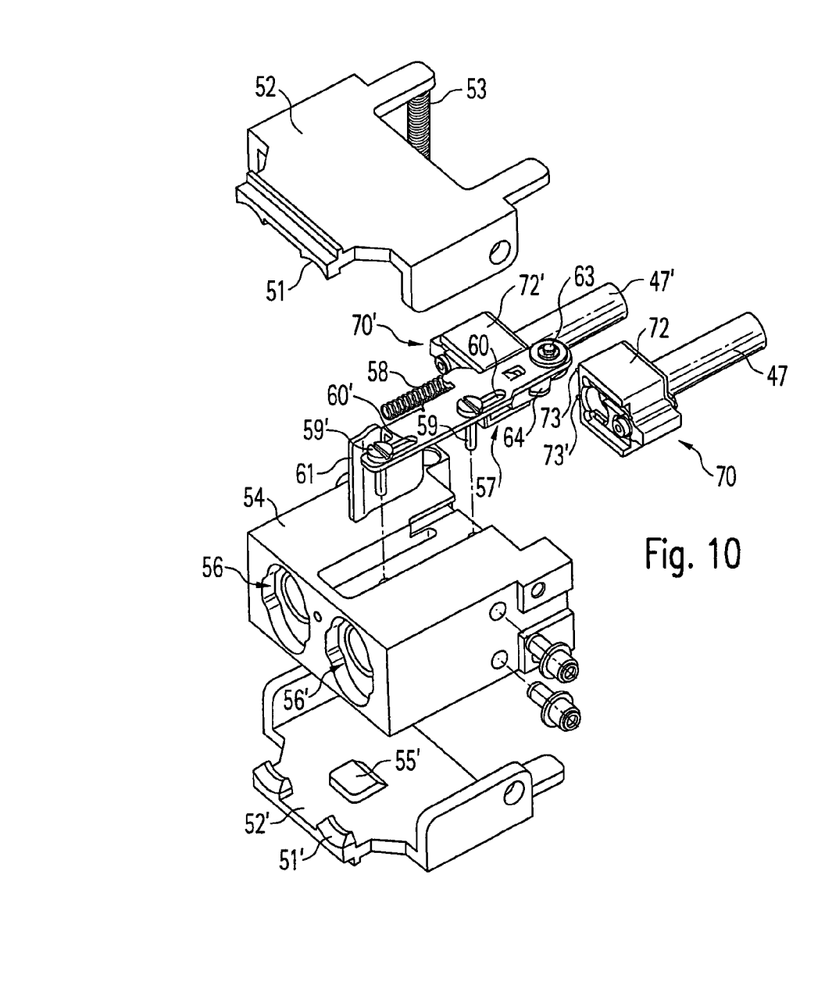
FIG. 10 is an exploded drawing of the holding device showing its functional elements.

The jaw holders 52, 52'—as shown in FIG. 4—are positioned on the frame 65 via swivel pins and pretensioned in the closed position (FIGS. 4-6) by means of springs 53 (see FIG. 10). In order to insert a pump unit 20 this is pushed into the holding device 50 in such a way that the jaws 51, 51' slip with front inclined surfaces over the lugs 46 of the pump unit 20 and are forced onto it. When the pump unit 20 has then been fully pushed on, the jaw holders 52, 52' snap shut and the jaws 51, 51' hold the pump unit 20 in this position until they are pushed apart again.

Figures 11, 12:
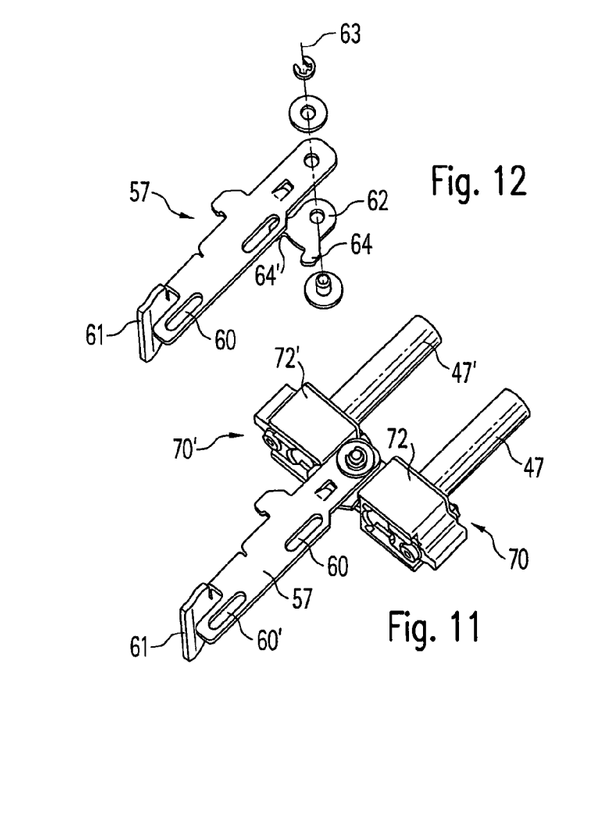
FIG. 11 is a perspective diagram of a sub-unit shown in FIG. 10.
FIG. 12 is an exploded drawing of the sub-unit shown in FIG. 11.

The mechanism for opening the holding device 50 or jaws 51, 51' is explained with the aid of FIGS. 10-12.

The holding device 50 encompasses a holding block 54, which has cylinder housings 56, 56' at its front which correspond to the rears of the cylinders 21, 21' of pump unit 20. The fit can be seen easily when FIGS. 2 and 10 are compared.

An opening slide 57 is fixed with fastening screws 59, 59' to the cylinder housing 56, whereby the opening slide 57 has elongated holes 60, 60' so that it can be pushed back and forth. The opening slide 52 is pushed backwards, away from the pump unit 20, by means of a spring 58.

A rocker 52 which can be swiveled back and forth is fixed to the opening slide 57 by means of a rocker bearing 63 carrying symmetrically arranged tongues 64, 64'. The opening slide 57 has an opening tongue 61 at its front, facing the pump unit 20. The opening tongue 61 has a height which corresponds to the distance between the internal surfaces of the jaw holders 52, 52'. On these inner surfaces of the jaw holders 52, 52' opening ramps 55, 55' have been attached in the displacement path of the opening tongue 61 in such a way that the opening tongue 61, on meeting the opening ramps 55, 55' and during further displacement in the direction of the pump unit 50, pushes apart the jaw holders 52, 52', so that they change from the position shown in FIGS. 4-6 to the position in FIGS. 7-9. In this position (according to FIGS. 7-9) the jaws 51, 51' disengage from the lugs 46 on the pump unit 20 thus releasing it. Displacement of the opening slide 57 occurs as described as follows.

Figure 6:
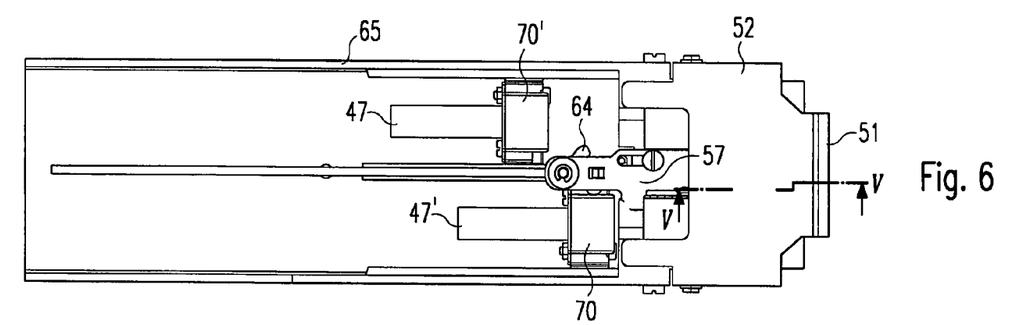
FIG. 6 is a plan view of the holding device shown in FIG. 4.
Figure 7:
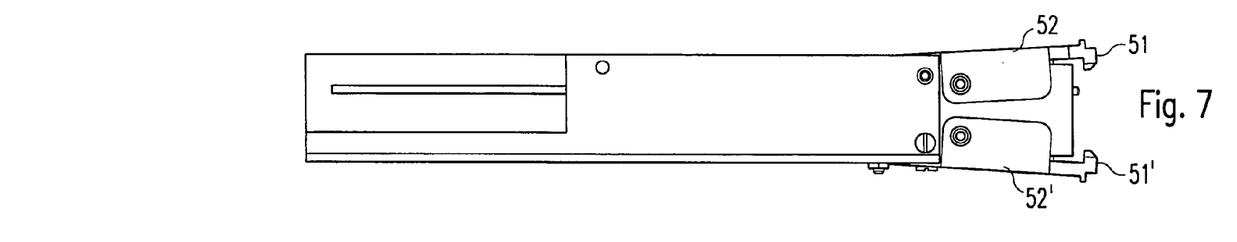
FIGS. 7-9 are views similar to illustrations corresponding to those in FIGS. 4-6, showing the holding device in an open position.
Figure 8:
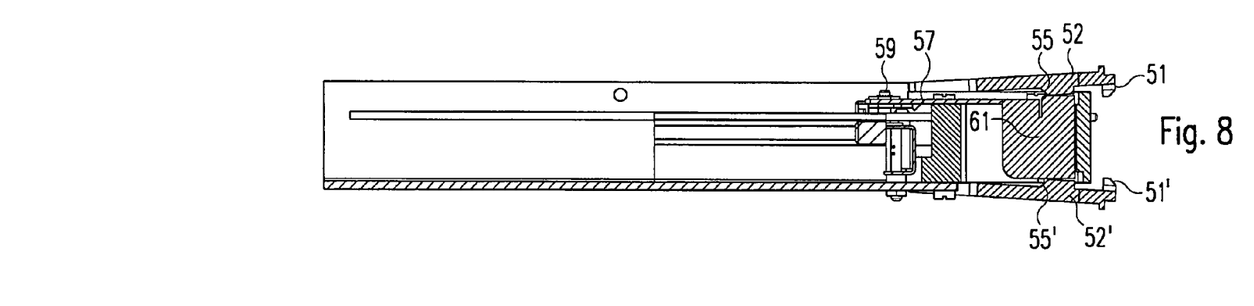
Figure 9:
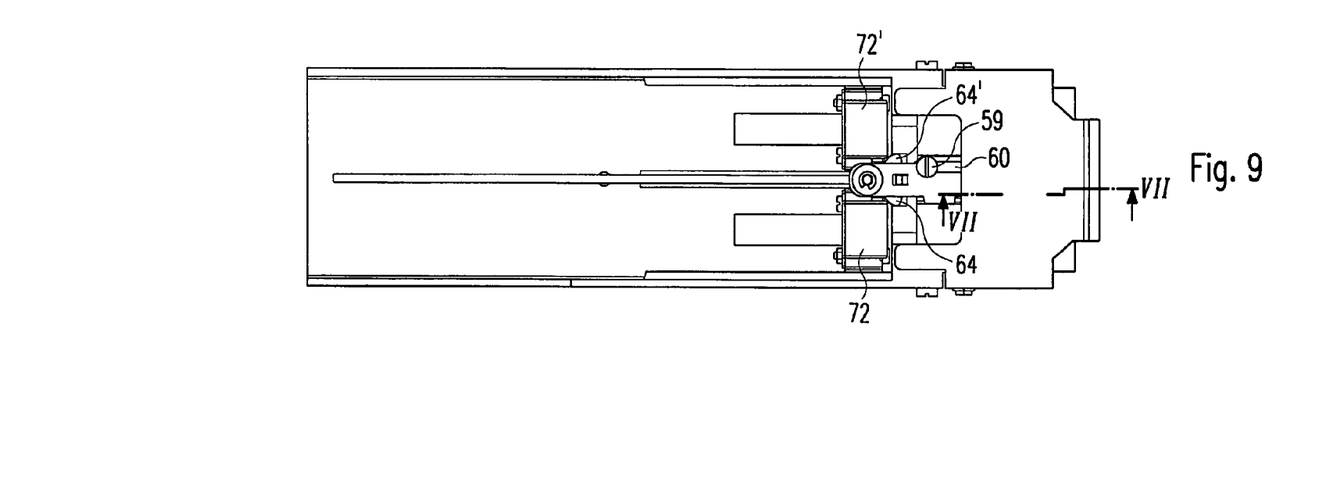
Figure 17:
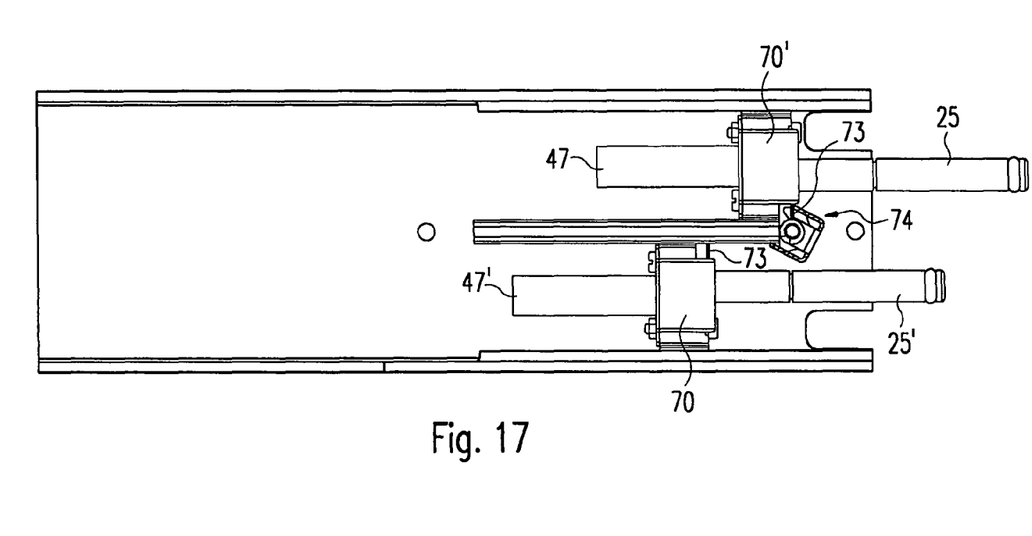
FIG. 17 is a plan view of the clutch means shown in FIG. 13 with coupled piston rods.
Figure 18:
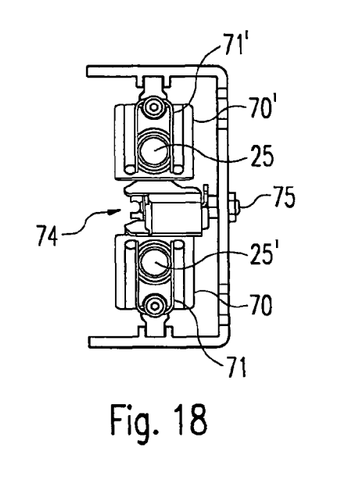
FIG. 18 is a front elevation of the clutch means shown in FIG. 17.
Figure 19:
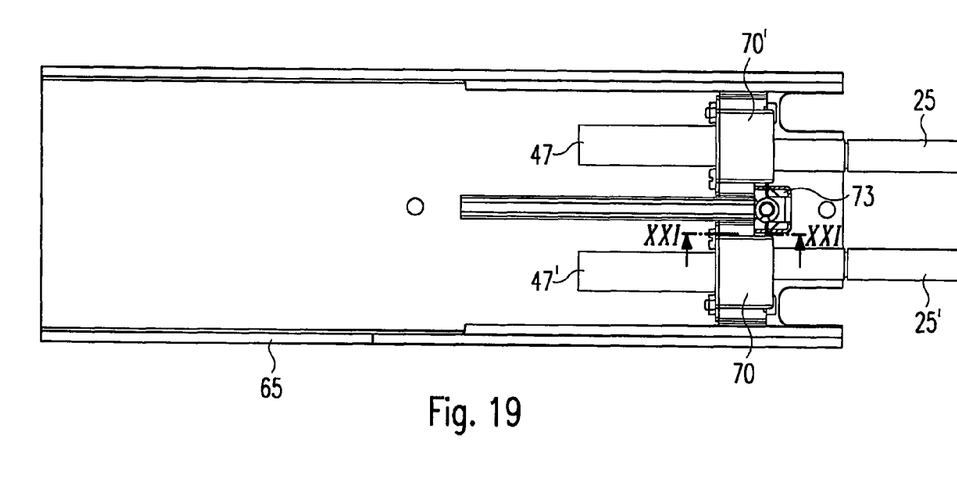
FIG. 19 is a view similar to FIG. 17, showing the clutch means in a different operational state.

During a "normal" operation of the pump unit 20 the shafts 47, 47' are moved back and forth alternately, so that in an end position of a shaft 47 or 47' they hold the positions shown in FIG. 6 or 17. During these movements the holding blocks 72, 72' are moved by the piston holders 70, 70' at the end of the shafts 47, 47' past the tongues 64, 64' in such a way that the rocker 62 is either tilted anti-clockwise, as shown in FIG. 6, or in the other direction in which the holding blocks 72, 72' are in the reverse position—projecting or pulled back, as shown in FIG. 17. These alternating movements of the piston holders 70, 70' or the holding blocks 72, 72' can thus be carried out to operate the pump without displacing the opening slide 57 in the direction of the pump unit 20.

But when the shafts 47, 47' are driven in such a way that both piston holders 70, 70' or holding blocks 72, 72' run side by side, the rocker 62 cannot be avoided during displacement (in the direction of the pump unit 20), so that both holding blocks 72, 72' engage simultaneously with both holding tongues 64, 64'. As a result the opening slide 57 is pushed against the force of the spring 58 in its elongated holes 60, 60' in the direction of the pump unit 50 when the piston holders 70, 70' continue to move forward so that the opening tongue 61 slides over the opening ramps 55, 55' thus forcing the jaw holders 52, 52' apart. The engagement of the jaws 51, 51' in relation to the lugs 46 on the pump unit 20 is released as a result. This opening of the holding device 50 thus occurs exclusively by means of the motors 11, 11' and their corresponding control by means of the motor control 15.

Below the effect or actuation of the clutch systems 13, 13' is described in more detail with which the piston rods 25, 25' are coupled to the piston holders 70, 70' via their coupling projections 17, 17'. Attention is drawn in this respect to FIGS. 13-21.

Figure 15:
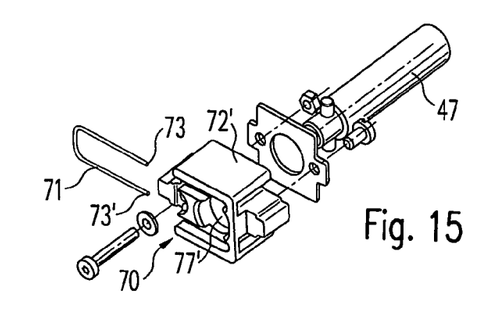
FIG. 15 is an exploded view of one clutch means shown in FIG. 13 and FIG. 14.
Figure 16:
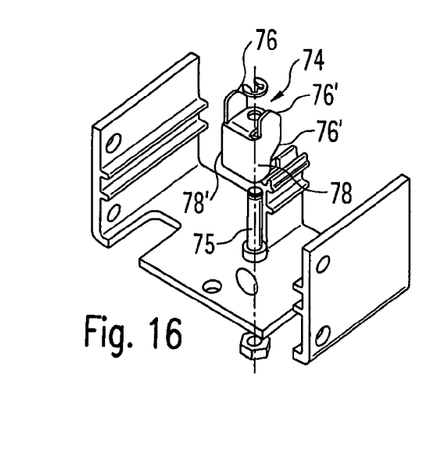
FIG. 16 is an exploded view of a sub-unit of the clutch means shown in FIG. 13.

The holding blocks 72, 72' are screwed onto the shafts 47, 47' as shown in FIG. 15 and comprise insertion openings 77, 77' into which the piston rods 25, 25' can be inserted with their coupling projections 17, 17'. Springs 71, 71' are attached to the holding blocks 72, 72' in such a way that the spring ends 73, 73' protrude into the insertion openings 77, 77'. The distance of the spring ends 73, 73' is such that the piston rods 25, 25' can be inserted into the insertion openings 77, 77' with their coupling projections 17, 17' and force the spring ends 73, 73' apart until they snap shut behind the coupling projections 17, 17'. For this the coupling projections 17, 17' have conical ends. After inserting the coupling projections 17, 17' into the piston holders 70, 70' the piston rods 25, 25' are connected to the piston holders 70, 70' and can neither be pushed nor pulled.

Between the displacement travel of the piston holders 70, 70' or the holding blocks 72, 72' a straddle lever 74 is attached on a swivel bearing 75 so that it can tilt, where on its upper and lower side it has straddle surfaces 76, 76' on the side facing away from the pump unit 20. On the other end, the end facing the pump unit 20, swivel edges 78, 78' are constructed on the straddle lever 74.

Figures 13, 14:
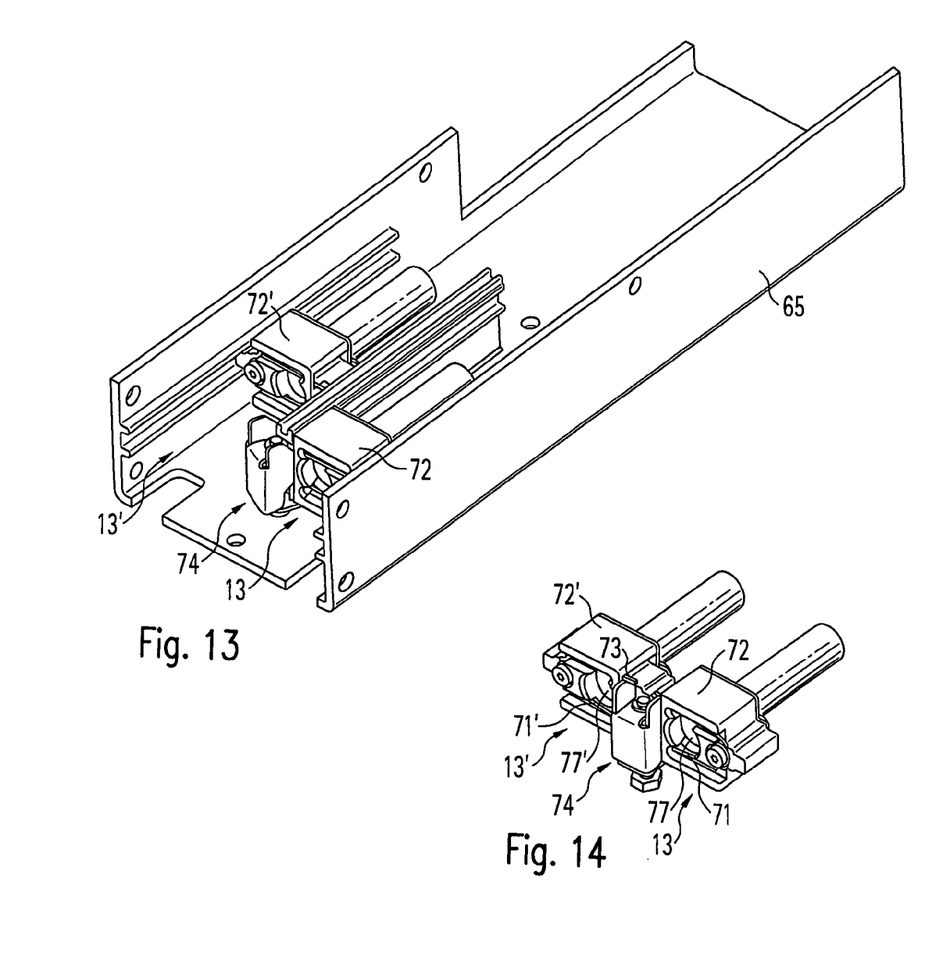
FIG. 13 is a perspective drawing of clutch means
FIG. 14 is a view of the clutch means shown in FIG. 13 in a different displacement position.
Figure 20:
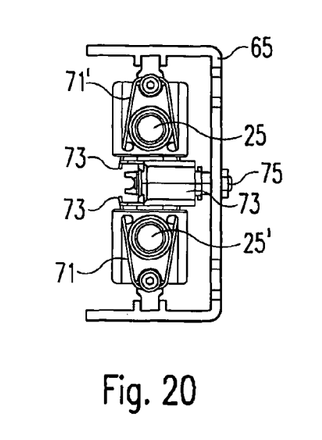
FIG. 20 is a front elevation of FIG. 19.
Figure 21:
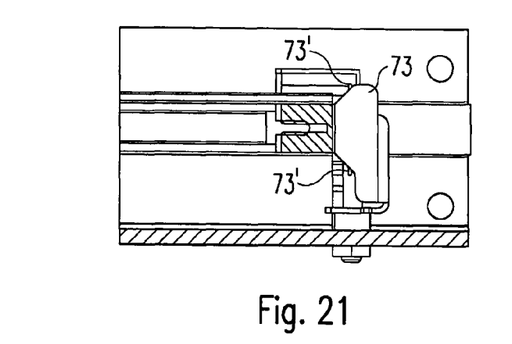
FIG. 21 is a section along line XXI-XI in FIG. 19.

The layout and dimensioning of the straddle lever 74 with its straddle surfaces 76, 76' and swivel edges 78, 78' is such that with alternating movements of the holding blocks 72, 72' or piston holders 70, 70', as shown in FIGS. 13 and 17, the straddle lever 74 is tilted either to one side or to the other side depending on which of the piston holders 70, 70' or holding blocks 72, 72' slide past it in the direction of the pump unit 20. As result of this swivel action, the straddle surfaces 76, 76' are swiveled in such a way that they do not engage with the spring ends 73, 73' of the piston holder 70 or 70' as they slide past. But when both piston holders 70, 70' are pushed parallel next to each other in the direction of the pump unit 20 (see FIGS. 14 and 19-21) the straddle surfaces 76 or 76' engage with the spring ends 73, 73' (see in particular FIGS. 20 and 21) so that these slide along on the (chamfered) straddle surface 76 or 76' and are forced apart. As a result of this forcing apart the piston rods 25, 25' previously attached to their coupling projections 17, 17' (see holding position according to FIG. 18) are released as shown in FIG. 20. After this with the same and simultaneous parallel movement of the piston holders 70, 70' or holding blocks 72, 72' the holding device 50 as well as the jaws 51, 51' are forced open and thus their engagement with the lugs 46 of the pump unit 20 is released, the pump unit can be removed by the parallel displacement of the piston holders 70, 70' as far as their front position facing the pump unit 20 without the user having to overcome any force.

The motor control 15 is furthermore constructed in such a way that after removal of a pump unit 20 from the pump actuating device 10, both shafts 47, 47' retract the piston holders 70, 70'. If the user inserts the pump unit 20 into the pump actuating unit 10, it is only the force required for opening the holding device 50 that needs to be overcome. The piston rods 25, 25' then protrude with their coupling projections 17, 17' through the cylinder housing 56, 56' into the pump actuating device 10. The user can now control the motor 15 in such a way that the same moves the piston holders 70, 70' in the direction of the pump unit 20 in a "coupling mode" until the coupling projections 17 or 17' push apart the spring ends 73, 73' and snap shut. This snapping process is carried out separately one after the other for both coupling projections 17 or 17', so that the straddle lever 74 does not open the springs 71, 71'.

In disclosed embodiments, coupling of the pump unit 20 to the pump actuating device 10 is partially accomplished and decoupling is completely accomplished by means of the drive, which is provided for actuation of the pump itself. Separate drive devices are therefore not required to operate the pump actuation and the coupling/decoupling.

The invention claimed is:
1. A medical pump comprising:
 a pump unit which is assembled as a single use article and which comprises two pistons and piston rods for displacing the pistons in allocated cylinders defined by the pump unit;

a pump actuating device comprising at least one controllable drive device and a motor control adapted to actuate the pump unit by displacing the two piston rods alternately;

holding devices which are adapted to open and close for reversible attachment of the pump unit to the pump actuating device; and clutch means which are adapted to open and close for reversible connection of the two piston rods to the at least one controllable drive device, wherein the at least one controllable drive device of the pump actuating device is further adapted to actuate the opening or closing of at least one of said holding devices or said clutch means, and wherein said at least one controllable drive device for said pump actuating device comprises motor means which operates to displace said pistons such that said pistons are displaced alternately during operation of the pump unit and synchronously during opening or closing of the holding device and/or the clutch devices.

2. The medical pump according to claim 1, wherein at least one of said holding devices or said clutch means comprises a snap device adapted to operate by snapping shut and open by means of said at least one controllable drive device opening said snap device.

3. The medical pump according to claim 2, wherein said snap device is constructed such that a force needed to close it is lower than a force needed to open it.

4. The medical pump according to claim 1, wherein said clutch means comprise engagement means which are fitted in said pump actuating device and which are positioned in a rest position prior to attachment of said pump unit to said pump actuating device whereby on connection of said pump unit to said pump actuating device the engagement means are disengaged from said piston rods and said clutch means is closable by actuation of said at least one controllable drive device.

5. The medical pump according to claim 1, wherein said at least one controllable drive device comprises a linear drive having at least one shaft and at least one motor for controllable driving of said the shaft.

6. The medical pump according to claim 1, wherein said motor control displaces said pistons at a constant speed.

* * * * *